United States Patent [19]

Doi et al.

[11] Patent Number: 4,665,081

[45] Date of Patent: May 12, 1987

[54] SOLID NIFEDIPINE PREPARATIONS AND A PROCESS FOR PREPARING SAME

[75] Inventors: Kengo Doi, Saitama; Shinichi Nitta, Tokyo; Masaki Kusakari; Nobuhiko Takahashi, both of Saitama, all of Japan

[73] Assignee: Takada Seiyaku Kabushiki Kaisha, Tokyo, Japan

[21] Appl. No.: 614,014

[22] Filed: May 25, 1984

[51] Int. Cl.$^4$ ............................................. A61K 31/44
[52] U.S. Cl. ................................................... 514/356
[58] Field of Search ........................ 424/266; 514/356

[56] References Cited

U.S. PATENT DOCUMENTS 3,862,332 1/1975 Barnhart et al. ..................... 424/337
4,412,986 11/1983 Kawata et al. ...................... 424/266

FOREIGN PATENT DOCUMENTS 3142853 5/1983 Fed. Rep. of Germany ...... 424/266
55-47615 4/1980 Japan ................................... 424/266

Primary Examiner—Allen J. Robinson
Attorney, Agent, or Firm—Birch, Stewart, Kolasch & Birch

[57] ABSTRACT

A new solid nifedipine preparation which comprises (a) a particulate dry composition having been obtained by subjecting nifedipine in mixture with casein and one or more inorganic excipients to co-pulverization or (b) a particulate dry composition having been obtained by adding an enteric high molecular substance and a plasticizer optionally with a higher fatty acid ester to the co-pulverized mixture obtained above, subjecting the mixture to co-pulverization and then dry-processing the co-pulverized product to a pharmaceutically acceptable solid form, as well as a process for preparing the solid nifedipine preparation comprising a particulate dry composition (a) or (b) by the specific co-pulverization and a dry compounding method. The solid nifedipine preparation is excellent in dissolution of nifedipine or possesses a controlled dissolution rate of nifedipine. This preparation is useful as a vasodilating medicament for the dual purposes of rapid and gradual release of nifedipine from the preparation for the remedy of angina pectoris or hypertension.

13 Claims, 8 Drawing Figures

SOLID NIFEDIPINE PREPARATIONS AND A PROCESS FOR PREPARING SAME

BACKGROUND OF THE INVENTION

1. Field of the Invention

The present invention relates to new solid nifedipine preparations useful as vasodilating agents and a process for preparing same. More particularly, the present invention relates to new solid nifedipine preparations useful as vasodilating agents and hypotensive medicaments which are excellent in dissolution of nifedipine and are capable of controlling the dissolution rate of nifedipine as well as a process for preparing same according to a specific dry compounding method.

2. Description of the Prior Art

Nifedipine (chemical name: dimethyl 2,6-dimethyl-4-(2-nitrophenyl)-1,4-dihydropyridine-3,5-dicarboxylate) possesses outstanding vasodilating activity, especially cardiovasodilating effect, and hypotensive activity and is thus utilized widely as a vasodilating agent and a hypotensive medicament clinically for the remedy of angina pectoris and hypertension. In general, this substance is administered to patients via an oral route. On the other hand, however, this substance has a disadvantage in being sparingly soluble in water so that it is extremely inferior in dissolution from its preparations manufactured by an ordinary pharmaceutical treatment, for example, processing with an excipient to granules or tablets, thus making it impossible to expect rapid absorption from digestive organs.

Proposed and actually adopted hitherto as a general means for enhancing dissolution of a sparingly soluble pharmacologically active substance from its solid preparations are (a) conversion of such substance into a soluble derivative thereof without affecting its pharmacological activity and the use of such soluble derivative as active substance, (b) fine pulverization of the substance on manufacture of its solid preparations, and (c) addition of a dissolution-promoting agent to the sparingly soluble active substance on manufacture of its solid preparations. In case of nifedipine, however, a satisfactory result has not yet been achieved by such generally adopted means. Concerning the means (a), for example, a water-soluble derivative of nifedipine has not yet been developed practically. In fact, no report is found in connection with such water-soluble derivative of nifedipine. In case of the means (b), the dissolution rate of nifedipine is not increased so remarkably by merely pulverizing it into very fine particles. Further, nifedipine in such finely particulate form is rather poor in stability. For example, Japanese Patent Publn. No. 59-14446 discloses a solid nifedipine preparation wherein nifedipine crystals having a specific surface area of 0.5–6 m$^2$/g have been mixed with a substantially inert pharmaceutically acceptable additive such as microcrystalline cellulose, lactose, starch and a surfactant. In this prior art, the gist thereof resides in the use of nifedipine crystals having a specific surface area. The individual ingredients are merely mixed for manufacturing the solid preparation. The dissolution rate of this preparation is not so high and the use of very fine nifedipine crystals having a specific surface area of more than 6 m$^2$/g is explained to be inferior in stability. In case of the means (c), the dissolution rate of nifedipine is only slightly increased even by adding a surfactant generally used as a dissolution-promoting agent, such as polyethylene glycol, polysolvate 80, sodium lauryl sulfate or polyoxyl 40 stearate. For example, Japanese Laid-open Patent Appln. No. 54-2316 discloses a solid nifedipine preparation wherein nifedipine has been blended with a surfactant such as sodium lauryl sulfate or with one or more additives such as cellulose derivatives, polyvinylpyrrolidone, urea and mannitol. This preparation is prepared by a wet method wherein the ingredients are dissolved and dispersed in an organic solvent and then the solvent is removed from the dispersion, for example, by spray drying or evaporation under reduced pressure. As a relatively large amount of an organic solvent is used in such wet method, this prior art involves problems such as protection of unstable nifedipine in the solvent from decomposition and troublesome treatments of a large amount of a solvent. In addition, dissolution of nifedipine from the preparation is not so remarkable. Experimentally, some of the dissolution-promoting agents were found to be effective to increase the dissolution rate of nifedipine when they were used in a larger amount. From the practical point of view, however, a considerable difficulty exists in developing a commercially attractive art for manufacturing a solid nifedipine preparation enhanced in dissolution of nifedipine from such experimental result.

Besides such solid nifedipine preparations, a liquid nifedipine preparation wherein nifedipine is dissolved in an organic solvent or a solid nifedipine preparation wherein nifedipine is adsorbed in a large amount of an excipient to form tablets are also known as attaining high dissolution of nifedipine. However, these preparations have also such a disadvantage that the size of the preparations, e.g. in the form of capsules or tablets becomes larger and thus dysphagic. For example, Japanese Patent Publn. No. 54-34048 discloses a liquid nifedipine preparation wherein nifedipine dissolved in an organic solvent such as polyalkylene glycol with a molecular weight of 200–4000 is enclosed in capsules. This preparation is chewable so that nifedipine dissolved in such organic solvent will be released from the capsule and rapidly absorbed in vivo. In such preparation, therefore, the concentration of nifedipine in blood plasma is increased rapidly after administration and the vasodilating effect is soon exhibited but the half-life period is very short, so that heart attack in the early morning and any side effect caused by rapid increase in the concentration of nifedipine in blood plasma cannot be prevented and duration of hypotensive activity can also be unexpected. Thus, it is generally desired not only to enhance dissolution of nifedipine as high as possible but also to maintain gradual dissolution of nifedipine for keeping nifedipine in blood plasma at a moderate therapeutic concentration.

From the past, coating of solid preparations in the form of granules, fine granules or tablets with an enteric high molecular compound or fat and oil to control release of the active ingredient has been proposed as a typical method for preparing activity-durable preparations. According to this method, an such enteric high molecular compound, fat and oil are dissolved in an organic solvent and the solution is applied as a thin film coating onto the surface of granules or tablets. Since this coating treatment requires a large amount of an organic solvent, this treatment is not suited for the case wherein the active ingredient in granules or tablets is unstable in or very sensitive to the organic solvent used. Thus, this coating method is not recommended for nifedipine. In some cases, a trace of a harmful organic solvent tends to remain as a residual solvent in the finished coatings. Thus, the use of an organic solvent for the coating treatment is not desirable for nifedipine preparations from the hygienic point of view and on the standpoint of energy-saving.

Under the above circumstances, there is still a great demand for developing solid nifedipine preparations which are excellent in dissolution of nifedipine and are capable of controlling the dissolution rate of nifedipine for assuring durable activity and which can be prepared according to a dry compounding method without using any liquid vehicle.

BRIEF SUMMARY OF THE INVENTION

Accordingly, it is an object of the present invention to provide a new-type solid nifedipine preparation which contains nifedipine in a co-pulverized specific form with other ingredients and is thus excellent in dissolution of nifedipine.

It is another object of the present invention to provide a hew-type solid nifedipine preparation which contains nifedipine in a doubly co-pulverized specific form with other ingredients and is thus excellent in dissolution of nifedipine but has a controlled dissolution rate enabling nifedipine to be maintained for a prolonged period of time at a high concentration in blood plasma.

It is still another object of the present invention to provide a process for preparing a new-type solid nifedipine preparation excellent in dissolution of nefedipine which comprises subjecting nifedipine to co-pulverization with other ingredients without using any liquid vehicle.

It is a further object of the present invention to provide a process for preparing a new-type solid nifedipine preparation having a controlled dissolution rate of nifedipine which comprises subjecting nifedipine to co-pulverization with other ingredients to form a co-pulverized mixture and subjecting it to co-pulverization with further ingredients.

Other objects, features and advantages of the present invention will become apparent more fully from the following descriptions.

DETAILED DESCRIPTION OF THE INVENTION

Figure 1:
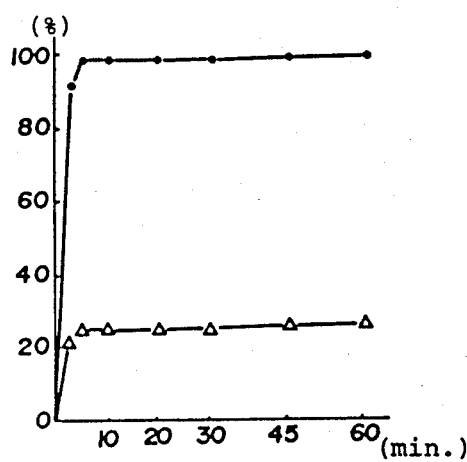

As a result of extensive studies of the present inventors on how to improve dissolution of nifedipine for developing a new solid nifedipine preparation possessing an enhanced dissolution rate of nifedipine, it has now been found that a fine particulate solid preparation of nifedipine which is excellent in dissolution of nifedipine can be obtained by mixing nifedipine with casein and one or more inorganic excipients and subjecting the mixture to co-pulverization without using any liquid vehicle. It has also been surprisingly found that a new solid nifedipine preparation which has a controlled dissolution rate of nifedipine and is thus assured of a durable vasodilating and hypotensive activities can be obtained by adding an enteric high molecular substance and a plasticizer optionally with a higher fatty acid ester to the co-pulverized product obtained in the above process, subjecting the mixture to further co-pulverization, and processing the doubly co-pulverized product to granules or tablets without using any liquid vehicle, or charging capsules with the doubly co-pulverized product. The present invention has been accomplished on the basis of the above findings.

By the term "co-pulverization (co-pulverize or co-pulverizing)" is meant herein the mode of pulverizing a substance, e.g. nifedipine, together with other ingredients at the same time, of course, without using any liquid vehicle. The co-pulverization of nifedipine with other ingredients was for the first time performed by the present inventors and is one of the characteristic features of the present invention. Thus, the present invention is apparently distinguished, for example, from the invention of Japanese Patent Publn. No. 59-14446 wherein the separately pulverized nifedipine is merely mixed with other ingredients optionally with the aid of a liquid vehicle.

In accordance with the present invention, there are provided new solid nifedipine preparations. In one embodiment thereof, the present invention provides a new solid nifedipine preparation which comprises a particulate dry composition having been obtained by subjecting nifedipine in mixture with casein and one or more inorganic excipients to co-pulverization.

The inorganic excipients used in the present invention are selected from the following inorganic compounds: magnesium silicate, magnesium carbonate, dried aluminum hydroxide gel, magnesium oxide, magnesium aluminate metasilicate, synthetic hydrotalcite and magnesium aluminum hydroxide.

Nifedipine itself is, as described hereinbefore, sparingly soluble in water and its solubility in water is reported as about 12 $\mu$g/ml. When nifedipine crystals alone are pulverized, the surface area of the crystal particles becomes larger so that the dissolution rate becomes higher. In the supersaturated state, however, it is difficult to dissolve nifedipine in water. Further, finely divided nifedipine crystals are searcely wetted with water. On the other hand, casein is hardly soluble in water. In a particulate binary composition obtained by co-pulverization of nifedipine and casein, there is found no special effect for enhancing dissolution of nifedipine. In a particulate composition obtained by co-pulverization of nifedipine and one or more of the above mentioned inorganic excipients, there is also found no special effect for enhancing dissolution of nifedipine.

In the solid nifedipine preparation of this invention, it is indispensable for enhancing dissolution of nifedipine that the particulate composition has been obtained by subjecting nifedipine in mixture with casein and one or more inorganic excipients to co-pulverization. The specific dissolution-promoting effect can not be expected if the inorganic excipients used in this invention are replaced by similar other inorganic excipients such as aluminum silicate, calcium carbonate, alumina and silica gel. Similarly, such dissolution-promoting effect can not be expected if the three essential ingredients, i.e. nifedipine, casein and one or more of the inorganic excipients are separately pulverized and then mixed together, or even if any one of the three essential ingredients is separately pulverized and mixed with a co-pulverized mixture of the other ingredients. At this stage, it is impossible to explain the reason why the dissolution of sparingly soluble nifedipine is enhanced by co-pulverizing nifedipine with casein and one or more specific inorganic excipients. It is supposed, however, that increase in the dissolution rate of nifedipine by co-pulverization with casein and one or more specific excipients is caused by the phenomenon that the crystalline nifedipine is probably rendered non-crystalline by such co-pulverization. As a non-crystalline substance is kept in a high energic state in solids, it is provided with good solubility. In case of crystalline nifedipine alone, crystallinity still remains even if it is pulverized finely. In general, it is difficult to make a crystalline organic compound alone non-crystalline. It is difficult to measure the particle size of the co-pulverized mixture exactly, since the mixture includes the ingredients in various particle sizes. In an event, an increase in the dissolution rate of nifedipine can be attained irrespective of the particle sizes of the co-pulverized mixture. Although some of the ingredients used in this invention, for example, certain kinds of the inorganic excipients are already used in the conventional nifedipine preparations, the co-pulverization of nifedipine with other specific ingredients and the unique effect achieved thereby have not yet been proposed in the prior arts. Thus, the present invention provides in this respect a new-type solid nifedipine preparation.

In the solid nifedipine preparation of this invention, the proportion of the three essential ingredients may be varied within a wide range according to the sort of the ingredients. In general, however, 0.2–9 parts by weight, preferably 0.3–5 parts by weight of the inorganic excipients and at least 0.5 part by weight, preferably 1.5–20 parts by weight of casein are used per part by weight of nifedipine.

If desired, one or more water-soluble saccharides may be added as ordinary organic excipients to the above essential ingredients prior to co-pulverization. By addition of such water-soluble saccharide to the ingredients, the operation for the co-pulverization becomes easier and the amounts of the ingredients to be mixed with nifedipine may be decreased. Illustrative of the water-soluble saccharide are, for example, glucose, fructose, mannitol, sorbitol, xylitol, maltose, lactose and sucrose. When one or more of the water-soluble saccharides are added to the essential ingredients, the amount of the whole saccharides is usually up to 6 parts by weight per part by weight of nifedipine. If 6 parts by weight of one or more water-soluble saccharides are added as organic excipient, the amounts of casein and the inorganic excipient per part by weight of nifedipine can be reduced to at least 0.1 part by weight, preferably 0.2–10 parts by weight and 0.15–7 parts by weight, preferably 0.15–3 parts by weight, respectively. It follows that the amount of casein can be varied from 0.1 part by weight to 20 parts by weight and that of the inorganic excipient can be varied from 0.15 part by weight to 9 parts by weight per part by weight of nifedipine according to the absence or presence of the optional water-soluble saccharide. If the amount of casein and/or the inorganic excipient is outside the above defined range, the effect of the co-pulverization on increase in the dissolution rate of nifedipine will be minimized or lost.

In another embodiment of the present invention, there is provided a new solid nifedipine preparation which comprises a particulate dry composition having been obtained by subjecting nifedipine in mixture with casein and one or more inorganic excipients to co-pulverization, adding an enteric high molecular substance and a plasticizer optionally with a higher fatty acid ester to the resultant co-pulverized mixture, subjecting the mixture to co-pulverization and then dry-processing the co-pulverized product to a pharmaceutically acceptable solid form.

The mixture obtained by the first co-pulverization is identical with the product obtained in the preceding embodiment. Thus, the inorganic excipients referred to above are also identical with those mentioned in the preceding embodiment and the proportion of casein and the inorganic excipients to nifedipine in this embodiment is also identical with that referred to in the preceding embodiment. In this embodiment, the product (i.e. the co-pulverized mixture) of the preceding embodiment is further incorporated with an enteric high molecular substance and a plasticizer optionally with a higher fatty acid ester and then again subjected to co-pulverization and the resultant co-pulverized product is then processed according to a method known per se to a pharmaceutically acceptable solid form such as granules, fine granules, tablets, dragees or capsules.

The enteric high molecular substance utilizable in this embodiment is selected from cellulose acetate phthalate, hydroxypropylmethylcellulose phthalate, methyl methacrylate copolymer, polyvinyl acetate phthalate, cellulose acetate succinate and styrene-maleric acid copolymer, among which cellulose acetate phthalate and hydroxypropylmethylcellulose phthalate are preferable.

The plasticizer utilizable in this embodiment is selected from polyethylene glycol (normally solid at room temperature), triacetin, polyoxyethylene sorbitan monooleate, propylene glycol and acetylated monoglyceride, among which solid polyethylene glycol with an average molecular weight of 4000–20000 is preferable.

The higher fatty acid ester optionally used together with the enteric high molecular substance and the plasticizer in this embodiment is selected from sucrose fatty acid ester, sorbitan fatty acid ester and glycerin fatty acid ester, among which sucrose fatty acid ester is preferable. In this case, the fatty acid moiety is derived from long chain fatty acids with 6–18 carbon atoms and the ester has an HLB value of 1–8, preferably 1–2.

The proportion of the enteric high molecular substance and the plasticizer to the co-pulverized mixture may be varied within a wide range according to the sorts of them used. In general, however, at least one part by weight, preferably 1.3–2.3 parts by weight of the enteric high molecular substance and at least 0.1 part by weight, preferably 0.13–0.38 part by weight of the plasticizer are used per part by weight of the co-pulverized mixture. If desired, the mixture comprised of the co-pulverized mixture, the enteric high molecular substance and the plasticizer may further be incorporated with the higher fatty acid ester. In this case, the higher fatty acid ester such as sucrose fatty acid ester is added to the mixture in an amount of at least 2% by weight, preferably 6–12% by weight based on the mixture.

In general, the enteric high molecular substances and the plasticizers are usually dissolved in an organic solvent and are coated as a thin film on the surface of a conventional solid nifedipine preparation in the form of granules or tablets. In this case, the enteric coating on the nifedipine preparation serves to protect it from disintegration by the action of gastric juice which is acidic and corresponds to a diluted HCl solution having a pH value of 1.2 so that rapid dissolution of nifedipine is prevented. If the enteric coating on the conventional nifedipine preparation is damaged by mechanical shock or unexpected external force, it will no longer be possible to inhibit rapid dissolution of nifedipine. In the solid nifedipine preparation of this invention, however, the enteric high molecular substance and the plasticizer are not coated as a thin film on granules or tablets containing nifedipine so that there is no fear of damage of the thin film. In the solid nifedipine preparation of this invention the enteric high molecular substance and the plasticizer are present in doubly co-pulverized form with nifedipine but the rapid dissolution of nifedipine is satisfactorily inhibited as in the case of a nifedipine preparation having enteric coatings.

If the proportion of the enteric high molecular substance and/or the plasticizer to the co-pulverized mixture is outside the above defined range, the effect on inhibiting rapid dissolution of nifedipine, or in other words, on gradual release of nifedipine from the preparation for an prolonged period of time will be minimized or lost. The dissolution rate of nifedipine from the preparations can properly be controlled by adjusting the amount of the higher fatty acid ester, such as sucrose fatty acid ester, having an HLB value of 1–8, preferably 1–2, as will be evident from Test Example 2.

In accordance with the present invention, there is also provided a process for the preparation of the new solid nifedipine preparations. In one embodiment thereof, the present invention provides a process for the preparation of a new solid nifedipine preparation, which comprises subjecting nifedipine in mixture with casein and one or more inorganic excipients optionally with a water-soluble saccharide to co-pulverization in a mill in the absence of any liquid vehicle.

In another embodiment of the prosess, there is provided a process for the preparation of a new solid nifedipine preparation, which comprises the steps of subjecting nifedipine in mixture with casein and one or more inorganic excipients optionally with a water-soluble saccharide to co-pulverization in a mill, adding an enteric high molecular substance and a plasticizer optionally with a higher fatty acid ester to the resultant co-pulverized mixture, subjecting the mixture to co-pulverization in a mill and then dry-processing the co-pulverized product to a pharmaceutically acceptable solid form, the treatments being conducted in the absence of any liquid vehicle throughout the steps.

All the ingredients and proportions thereof used in the two embodiments of the process have been described hereinbefore. The process is distinguished by using no liquid vehicle for the mixing and co-pulverizing treatments throughout the steps.

In the firstly mentioned process, nifedipine is mixed with given amounts of casein and one or more inorganic excipients and the mixture is subjected to co-pulverization in a mill at ambient temperature. The time required for the co-pulverization varies according to the sorts of the ingredients, proportion thereof and the sort of the mill used, but is usually within the period from 60 minutes to 180 minutes.

The co-pulverization of the ingredients is carried out according to an ordinary operation for dry pulverization of solid substances except that the ingredients are pulverized at the same time in a mixed state. Any type of mills utilizable for finely dividing solid substances in dry mode can be used for the co-pulverization, such as various types of ball mills, rod mills, hammer mills and jet mills among which ball mills, especially vibrating ball mills are preferred. In case of using a vibrating ball mill, the co-pulverization operation is usually finished within the period from 90 minutes to 120 minutes at room temperature. The condition for the co-pulverization can be varied or established according to a result of the dissolution test as will be referred to hereinafter.

The co-pulverized mixture thus obtained is then mixed in a usual manner with conventional additives such as a disintegrating agent, a binder, a lubricant and the like excipients and the mixture is then processed according to the method known per se to a pharmaceutically acceptable form, especially for oral applications, such as powdery agents, granules, fine granules, tablets, dragees and capsules. Illustrative of the additive are, for example, corn starch, potato starch, CMC, MC, polyvinylpyrrolidone, light silicic anhydride, calcium carbonate, magnesium stearate, gum arabic and lactose.

In the secondly mentioned process wherein the co-pulverization treatment is performed twice, the first co-pulverization step is quite identical with the firstly mentioned process. Thus, the conditions adopted for the firstly mentioned process are just applied to this process. The resultant co-pulverized mixture is then mixed with given amounts of the enteric high molecular substance and the plasticizers. These ingredients to be mixed with the co-pulverized mixture may be single substances or in a mixture of more than one. If desired, the resultant mixture may be incorporated with the higher fatty acid ester which may be a single compound or a mixture or more than one, thereby suitably controlling the dissolution rate of nifedipine. The mixture is then subjected to the second co-pulverization treatment which, as remarked in the first co-pulverization treatment, is conducted in the same manner as in the firstly mentioned process.

The doubly co-pulverized product thus obtained is then processed, in the same manner as described above, to a pharmaceutically acceptable form, especially for oral applications. These treatments are wholly conducted in the absence of any liquid vehicle.

The solid nifedipine preparations obtained in the firstly mentioned process are excellent in dissolution of nifedipine as will be evident from results of the dissolution tests. As dissolution of nifedipine is high in the preparation of this invention, the present invention can provide tablets and capsules smaller in size.

On preparation of the solid nifedipine preparations, it is necessary that the resultant preparations give a dissolution rate of at least 95% according to the dissolution test No. 2 (Paddle method) of the Japanese Pharmacopeia, X. Thus, the conditions for the co-pulverization and the proportion of nifedipine to the other ingredients can suitably be modified in view of the result of the dissolution test.

The solid nifedipine preparation obtained according to the secondly mentioned process, which has a controlled dissolution rate of nifedipine as will be evident from the Test Examples, exhibits excellent durable effect on dissolution of nifedipine besides an improved dissolution rate of nifedipine, as compared with a similar solid nifedipine preparation obtained with the co-pulverization of the ingredients.

Accordingly, the two types of the solid nifedipine preparations are useful as a vasodilating medicament of dual action (rapid and gradual release of nifedipine from the preparations) for the remedy of angina pectoris or hypertension. As the process for preparing the solid nifedipine preparations involves no necessity of using any liquid vehicle, the process can be relieved from troublesome treatments for dealing with the liquid vehicles and is advantageous from the economical and hygienic points of view.

The present invention will now be illustrated in more detail by way of the following Examples and Test Examples wherein the term "the Japanese Pharmacopeia" will be referred to as "J.P.".

EXAMPLE 1

Using a vibrating ball mill (Chuo Kakoki Kogyo KK, Japan, Model MB-50), a mixture comprising 0.5 kg of nifedipine, 0.75 kg of casein (food-additive grade) and 0.5 kg of magnesium silicate (J.P.) was subjected to co-pulverization. The co-pulverization operation was carried out by charging a container of a capacity of 158 l with 13,000 balls made of alumina and having a diameter of 20 mm and then with the mixture and effecting the co-pulverization for 120 minutes. To this co-pulverized mixture were then added 23 kg of lactose and 0.25 kg of magnesium stearate. The mixture was subjected to granulation by the aid of a dry granulating machine (a roller compactor Model TF-156, Freund Ind. Co., Ltd., Japan) to manufacture fine granules containing nifedipine in an amount of 20 mg/g. Dissolution of the resultant fine granules was examined according to the dissolution-testing method No. 2 (Paddle method), J.P.X. whereby the granules showed good dissolution and a dissolution rate as high as 98% was obtained after 5 minutes. FIG. 1 shows dissolution curves of the fine granules (A) manufactured from the co-pulverized mixture and the fine granules (B) manufactured from a mixture of the individually pulverized ingredients. In FIG. 1, the abscissa stands for the dissolution time in terms of minute while the ordinate for the dissolved quantity of nifedipine in terms of percentage and the curve shown by—●—●—stands for the granules (A) while the curve shown by—Δ—Δ—for the granules (B).

The dissolution test was carried out in the following manner: As a liquid for the test was used 200 ml of water. A sample in an amount corresponding to 10 mg of nifedipine was added to the liquid while maintaining it at 37°±0.5° C. A paddle was rotated at 100 r.p.m. in the liquid and a small volume of the liquid containing the dissolved nifedipine was taken out at given time intervals and filtered through a glass filter (G3). The filtrate (5 ml) was extracted with ether and the ether was distilled off from the ethereal extract. Methanol (5 ml) was added to the residue and determination of nifedipine dissolved in the methanol was then carried out according to UV-spectrophotometry ($\nu=350$ nm).

It was observed that the fine granules manufactured from the co-pulverized mixture scarcely showed any decrease in dissolution rate even after allowed to stand for 6 months at 40° C. and 75% R.H. in an air-tight container.

EXAMPLE 2

Figure 2:
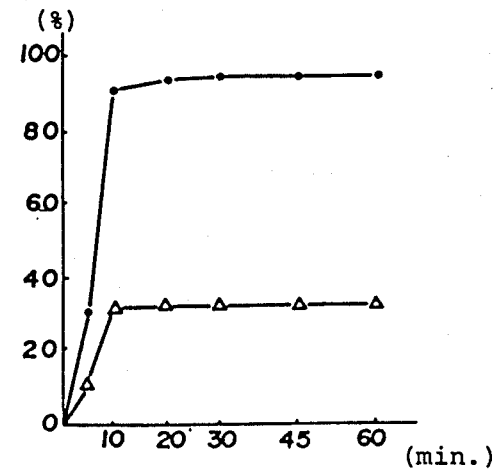

Using a vibrating rod mill (Hirako Mfg. Works, Japan, Model TI-200), a mixture comprising 1 g of nifedipine, 1.5 g of casein (the same grade as in Example 1) and 5 g of magnesium aluminate metasilicate (Neusilin, Fuji Chem. Ind. Co., Ltd., Japan) was subjected to co-pulverization. The co-pulverization operation was carried out by charging a container having a capacity of 307 ml with rods made of alumina and having a length of 6.5 cm and a diameter of 4.5 cm and then with the mixture and effecting the co-pulverization for 90 minutes. This co-pulverized mixture was admixed homogeneously with 5.37 g of potato starch and 0.13 g of magnesium stearate and the subjected to capsulation by the aid of a capsule charger to manufacture hard capsules each containing 130 mg of the co-pulverized mixture (10 mg as nifedipine). Dissolution of the hard capsules thus obtained was examined according to the dissolution-testing method No. 2 (Paddle method), J.P.X. whereby the hard capsules showed good dissolution and dissolution rates of 90% and 94% were obtained after 10 minutes and 45 minutes, respectively. FIG. 2 shows dissolution curves of the hard capsules (A) manufactured from the co-pulverized mixture and the hard capsules (B) manufactured from a mixture of the same composition as in the co-pulverized mixture, which had been prepared by co-pulverizing nifedipine and casein, adding pulverized magnesium aluminate metasilicate to the resultant mixture and blending potato starch and magnesium stearate therewith. In FIG. 2, the abscissa stands for the dissolution time in terms of minute while the ordinate for the dissolved quantity of nifedipine in terms of percentage and the curve shown by—●—●—stands for the capsules (A) while the curve shown by—Δ—Δ—for the capsules (B).

The dissolution test was carried out in the following manner: As a liquid for the test was used 200 ml of 0.1 N hydrochloric acid having a pH value of 1.06. One capsule (10 mg as nifedipine) was dipped into the liquid with the aid of a sinker while maintaining the liquid at 37°±0.5° C. and the subsequent treatments were carried out in the same manner as described in Example 1.

It was observed that the capsules manufactured from the co-pulverized mixture scarcely showed any decrease in dissolution rate even after allowed to stand for 6 months at 40° C. and 75% R.H. in an air-tight container.

EXAMPLE 3

Figure 3:
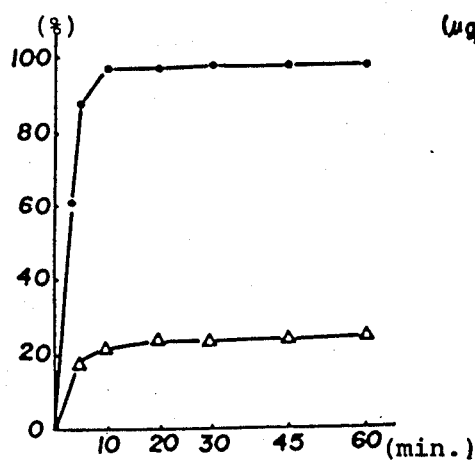

A mixture of 0.5 kg of nifedipine, 0.25 kg of casein (identical with that used in Example 1), 0.5 kg of magnesium silicate (identical with that used in Example 1) and 2.5 kg of lactose was subjected to co-pulverization under the same conditions as illustrated in Example 1. To this co-pulverized mixture were added 2.779 kg of corn starch, 0.146 kg of light silicic anhydride, 0.75 kg of carboxymethylcellulose (NS-300, marketed from Gotoku Yakuhin KK, Japan) and 0.075 kg of magnesium stearate, and the whole was homogeneously mixed and then processed to tablets each weighing 150 mg and containing 10 mg of nifedipine by the aid of a rotary tablet press (Hata Tekkosho, Japan, Model HT.AP3-8SIII). Dissolution of the tablets thus obtained was examined according to the dissolution-testing method No. 2 (Paddle method), J.P.X. whereby the tablets showed good dissolution and dissolution rates of 90% and 98% were obtained after 5 minutes and 20 minutes, respectively. FIG. 3 shows dissolution curves of the tablets (A) manufactured from the co-pulverized mixture and the tablets (B) manufactured from a mixture of the same composition as in the co-pulverized mixture, which had been prepared by co-pulverizing nifedipine and magnesium silicate, adding to the resultant mixture the individually pulverized casein and lactose and adding corn starch, light silicic anhydride, carboxymethylcellulose and magnesium stearate to the mixture. In FIG. 3, the abscissa stands for the dissolution time in terms of minute while the ordinate for the dissolved quantity of nifedipine in terms of percentage and the curve shown by—●—●—stands for the tablets (A) while the curve shown by—Δ—Δ—for the tablets (B).

The dissolution test was carried out in the following manner: As a liquid for the test was used 200 ml of water. One tablet (10 mg as nifedipine) was dropped in the liquid while maintaining it at 37°±0.5° C. and the subsequent treatments were carried out in the same manner as described in Example 1.

Figure 4:
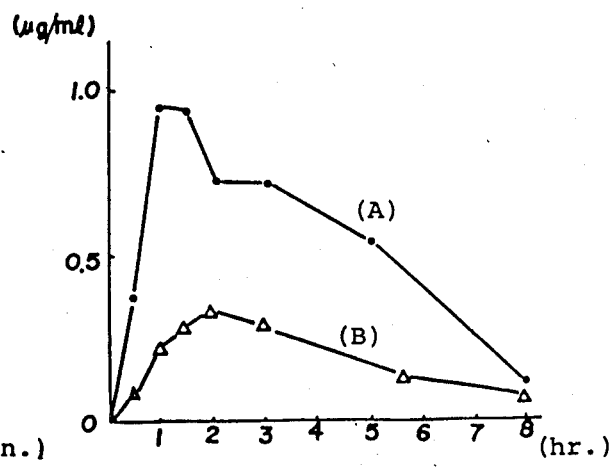

Using groups of a test animal, each group consisting of 4 rabbits (Japanese white strain) of 2.5–2.9 kg in body weight, the aforesaid tablets (A) and (B) were orally administered together with 30 ml of water to the rabbits in a dose of one tablet per rabbit (10 mg of nifedipine per rabbit). Blood was extracted from a vein in an ear region just after the administration and at the time of 0.5, 1, 1.5, 2, 3, 5 and 8 hours after the administration, and the concentration of nifedipine in the blood plasma was measured. A result of the measurement is shown in FIG. 4 (graph) as a concentration curve of nifedipine in blood plasma with the lapse of time wherein the ordinate stands for the concentration of nifedipine in blood plasma in terms of μg per ml of blood plasma while the abscissa stands for the elapsing time in term of hour after administration of the nifedipine tablet and wherein the curve shown by—•—•—stands for the tablets (A) while the curve shown by—Δ—Δ—for the tablets (B). In case of the tablet (A), nifedipine is rapidly absorbed after administration and is maintained at a higher concentration in blood for a long period of time as shown by the curve (A). In case of the tablet (B), on the contrary, nifedipine is absorbed slowly and is maintained at a lower concentration in blood after administration as shown by the curve (B). From these curves standing for the concentration of nifedipine in blood plasma with the lapse of time, areas under the curves (AUC) were calculated according to the trapezoidal rule whereby the area in case of the tablet (A) was 4.24 μg.hr/ml while that in case of the tablet (B) was 1.43 μg.hr/ml, thus showing advantage of the tablet (A) which is about 3 times as high in absorption as the tablet (B).

It was observed that the tablet (A) was stable and scarcely showed any decrease in dissolution rate even after allowed to stand in an air-tight container for 6 months at 40° C. and 75% R.H.

EXAMPLE 4

Using a vibrating ball mill (Chuo Kakoki Kogyo KK, Model MB-1), a mixture of 30 g of nifedipine, 45 g of casein (food-additive grade) and 30 g of magnesium silicate (J.P.) was subjected to co-pulverization. The co-pulverization operation was carried out by charging a container made of alumina having a capacity of 3.4 l with 200 balls made of alumina and having a diameter of 20 mm and 40 balls made of alumina and having a diameter of 30 mm and then with the mixture and effecting the co-pulverization for 120 minutes. To 42 g of this co-pulverized mixture were added 84 g of cellulose acetate phthalate (J.P.), 14.4 g of polyethylene glycol 6000 (J.P.) and 13.2 g of sucrose fatty acid ester (HLB 2, food-additive grade, Dai-ich Kogyo Seiyaku KK, Japan). Using the vibrating ball mill, the mixture thus obtained was co-pulverized for 20 minutes. The twice co-pulverized mixture was subjected to granulation by the aid of a dry granulating machine (a roller compactor Model TF-156, Freund Ind. Co., Ltd., Japan) to manufacture granules having a size of 16–30 mesh.

EXAMPLE 5

The granules of 16–30 mesh in size prepared according to the process illustrated in Example 4 was subjected to capsulation by the aid of a capsule charger to manufacture hard capsules each containing 128 mg of the granules (10 mg as nifedipine).

EXAMPLE 6

The granules (3.2 kg) of 16–30 mesh in size prepared according to the process illustrated in Example 4 was mixed with lactose (1.05 kg) and corn starch (2.45 kg) in a ratio of 3:7 and the mixture was subjected to granulation by the aid of a dry granulating machine (a roller compactor Model TF-156, Freund Ind. Co., Ltd., Japan) to manufacture granules of 20–50 mesh in size. To 3.5 kg of the granules thus obtained were added 0.75 kg of carboxymethylcellulose (NS-300, marketed from Gotoku Yakuhin KK, Japan) and 0.05 kg of magnesium stearate. The mixture was homogeneously mixed and then processed to tablets each weighing 300 mg and containing 10 mg of nifedipine by the aid of a rotary tablet press (Hata Tekkosho, Japan, Model HT-AP38S-III).

TEST EXAMPLE 1

Figure 5:
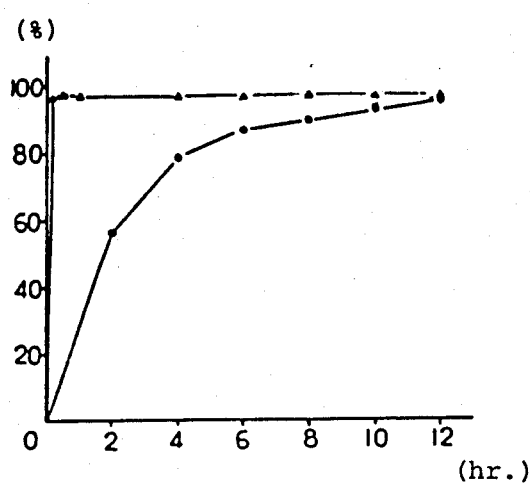

Dissolution of the granules obtained in Example 4 was examined according to the dissolution-testing method No. 2 (Paddle method), J.P.X. whereby it was confirmed that nifedipine was dissolved gradually over the period of about 12 hours. FIG. 5 shows dissolution curves of the granules (A) manufactured from the co-pulverized mixture and the granules (B) of 16–30 mesh in size manufactured by homogeneously mixing 184 g of lactose and 2 g of magnesium stearate with 70 g of a co-pulverized product (prepared by co-pulverizing 30 g of nifedipine, 45 g of casein and 30 g of magnesium silicate for 120 minutes under the same conditions illustrated in Example 4 by the aid of a vibrating ball mill) and granulating the mixture by the aid of a dry granulating machine (a roller compactor Model TF-156, Freund Ind. Co., Ltd., Japan). In FIG. 5, the abscissa stands for the dissolution time in terms of hour while the ordinate for the dissolved quantity of nifedipine in terms of percentage and the curve shown by—•—•—stands for the granules (A) while the curve shown by—Δ—Δ—for the granules (B).

The dissolution test was carried out in the following manner: As a liquid for the test was used 900 ml of a phosphate buffer solution having a pH value of 6.8. A sample in an amount corresponding to 10 mg of nifedipine was added to the liquid while maintaining it at 37°±0.5° C. A paddle was rotated at 100 r.p.m. in the liquid and a small volume of the liquid containing the dissolved nifedipine was taken out at given time intervals and filtered through a membrane filter (0.8μ in pore size). The filtrate (5 ml) was extracted with ether and the ether was removed by distillation from the ethereal extract. Methanol (5 ml) was added to the residue and determination of nifedipine dissolved in the methanol was then carried out according to UV-spectrophotometry ($\nu=360$ nm).

TEST EXAMPLE 2

A relation between the amount of sucrose fatty acid ester (HLB 2, food-additive grade, Dai-ichi Kogyo Seiyaku KK, Japan) added and the dissolution rate of nifedipine was examined. To 42 g of a co-pulverized mixture obtained by co-pulverizing a mixture of 30 g of nifedipine, 45 g casein and 30 g of magnesium silicate for 120 minutes under the same condition as illustrated in Example 4 were added 84 g of cellulose acetate phthalate, 14.4 g of polyethylene glycol 6000 and sucrose fatty acid ester (HLB 2) in an amount shown in Table 1. Granules of 16–30 mesh in size were manufactured from the above mixture according to the process illustrated in Example 4.

TABLE 1

| Ingredients | Compositions (parts by weight) | | | |
| --- | --- | --- | --- | --- |
| | a | b | c | d |
| Nifedipine | 10 | 10 | 10 | 10 |
| Casein | 15 | 15 | 15 | 15 |
| Magnesium silicate | 10 | 10 | 10 | 10 |
| Cellulose acetate phthalate | 70 | 70 | 70 | 70 |
| Polyethylene glycol (M.W. 6000) | 12 | 12 | 12 | 12 |
| Sucrose fatty acid ester (HLB 2) | — | 9 | 12 | 14 |

Figure 6:
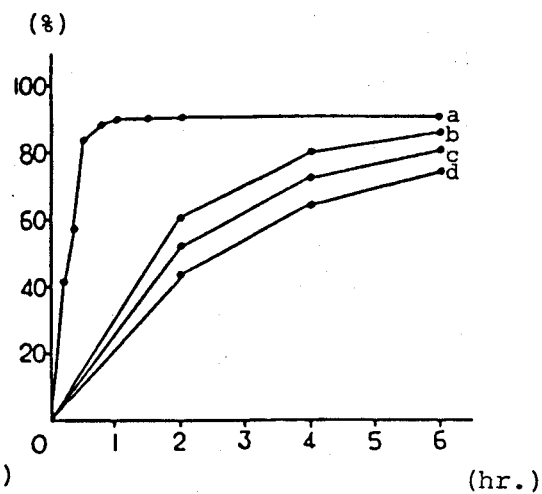

When dissolution of the granules having the compositions a, b, c and d shown in Table 1 (varying in the content of the sucrose fatty acid ester (HLB 2) was examined according to the dissolution-testing method No. 2 (Paddle method), J.P.X., it was confirmed that the dissolution rate of nifedipine could properly be controlled by varying the amount of the sucrose fatty acid ester (HLB 2). The dissolution test itself was carried out in the same manner as illustrated in Test Example 1. FIG. 6 shows dissolution curves of the granules having the compositions a, b, c and d, wherein the abscissa stands for the dissolution time in terms of hour and the ordinate for the dissolved quantity of nifedipine in terms of percentage.

TEST EXAMPLE 3

Figure 7:
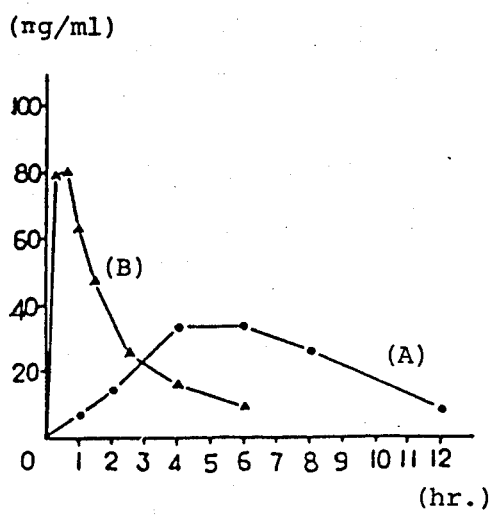

The hard capsules containing 10 mg of nifedipine which had been obtained according to the process as illustrated in Example 5 were orally administered to 6 healthy male adult volunteers in a dose of one capsule per volunteer, and change in the concentration of nifedipine in blood plasma with the lapse of time was then measured. A comparative test was also performed by using a commercially available similar soft capsule containing 10 mg of nifedipine as a control preparation. FIG. 7 shows a result of the measurement using the hard capsules as well as a result of the measurement in the comparative test using the soft capsules as an average value of the 6 volunteers, as a graph showing the change in concentration of nifedipine in blood plasma with the lapse of time, wherein the ordinate stands for the concentration of nifedipine in blood plasma in terms of ng per mol of blood plasma while the abscissa for the elapsing time after administration of the nifedipine preparations in terms of hour and wherein the curve (A) shown by —•—•— stands for the hard capsules while the curve (B) shownby —Δ—Δ— for the soft capsule as control.

From the result shown in FIG. 7, it is evident that the hard capsule preparations obtained according to the process as illustrated in Example 5 is gradually absorbed after administration as shown by the curve (A) so that nifedipine is still detected in blood plasma even after the lapse of 12 hours from the administration while the soft capsule preparation as control is rapidly absorbed after administration, as shown by the curve (B), but is shorter in the period of time for maintaining nifedipine in blood than the hard capsule preparation. The results of tests in vitro given in the foregoing Test Examples 1 and 2 and of tests in vivo given in this Test Example 3 apparently demonstrate that the solid nifedipine preparations of the present invention exhibit outstanding durable effects and indeed prolong the time for maintaining the concentration of nifedipine in blood at a given level.

TEST EXAMPLE 4

Dissolution of the granular preparation obtained according to the process as illustrated in Example 4 was examined according to the dissolution-testing method No. 2 (Paddle method), J.P.X., using the Liquid No. 1 (pH 1.2) and Liquid No. 2 (pH 6.8) in the disintegration-testing method, J.P.X. as test liquids whereby the granular preparation was found sparingly soluble in the Liquid No. 1, exhibiting a similar effect to the case of granular preparations having a coating on the surface of the granules, but was found gradually soluble in the Liquid No. 2.

The dissolution test was carried out in the following manner: As a liquid for the test was used Liquid No. 1 (pH 1.2) or Liquid No. 2 (pH 6.8) for the disintegration-testing method, J.P.X. A sample in an amount corresponding to 10 mg of nifedipine was added to the liquid while maintaining it at 37°±0.5° C. A paddle was rotated at 100 r.p.m. in the liquid and a small volume of the liquid containing the dissolved nifedipine was taken out at given intervals and filtered through a membrane filter (0.8μ in pore size). The filtrate (5 ml) was extracted with ether and the ether was distilled off from the ethereal extract. Ethanol (5 ml) was then added to the residue and determination of nifedipine dissolved in the ethanol was carried out according to UV-sepctrophotometry ($\nu=360$ nm).

Figure 8:
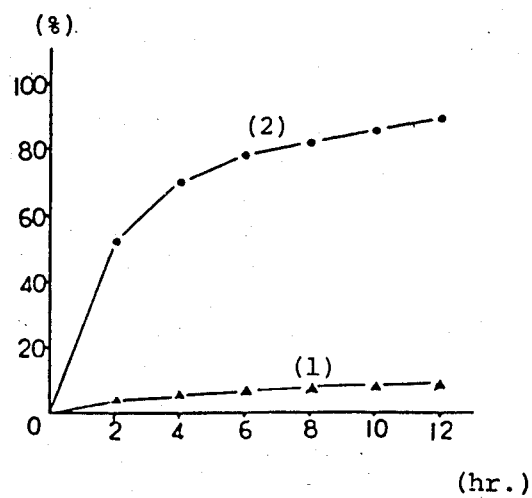

FIG. 8 is a graph showing dissolution curves of the granular preparation in the Liquid No. 1 and in the Liquid No. 2 wherein the curve (1) shows dissolution of nifedipine in the Liquid No. 1 while the curve (2) shows dissolution of nifedipine in the Liquid No. 2.

It is understood that the preceding representative embodiments may be varied within the scope of the present specification both as to ingredients as well as co-pulverization and mixing conditions, by those skilled in the art to achieve essentially the same results.

As many widely different embodiments of this invention may be made without departing from the spirit and scope thereof, it is construed that the present invention is not limited to the specific embodiments thereof except as defined in the appended claims.

What is claimed is:

1. A solid nifedipine preparation which comprises a particulate dry composition containing an effective vasodilating or hypotensive amount of nifedipine obtained by the process comprising subjecting nifedipine in mixture with casein and one or more inorganic excipients to co-pulverization in the absence of any liquid vehicle, said inorganic excipient being a member selected from the group consisting of magnesium silicate, magnesium carbonate, dried aluminum hydroxide gel, magnesium oxide, magnesium aluminate metasilicate, synthetic hydrotalcite and magnesium aluminum hydroxide.

2. A solid nifedipine preparation according to claim 1, wherein at least 0.5 parts by weight of casein and 0.2–9 parts by weight of said inorganic excipient are used per part by weight of nifedipine.

3. A solid nifedipine preparation according to claim 1, wherein 1.5–20 parts by weight of casein and 0.3–5 parts by weight of the inorganic excipients are used per part by weight of nifedipine.

4. A solid nifedipine preparation according to claim 1, wherein one or more water-soluble saccharides are added in an amount up to 6 parts by weight per part by weight of nifedipine.

5. A solid nifedipine preparation according to claim 4, wherein said saccharide is a member selected from the group consisting of glucose, fructose, mannitol, sorbitol, xylitol, maltose, lactose and sucrose.

6. A solid nifedipine preparation according to claim 5, wherein the pharmaceutically acceptable solid form is a member selected from the group consisting of granules, tablets, dragees and capsules.

7. A solid nifedipine preparation which comprises a particulate dry composition obtained by the process comprising subjecting nifedipine in mixture with casein and one or more inorganic excipients to co-pulverization in the absence of any liquid vehicle, said inorganic excipient being a member selected from the group consisting of magnesium silicate, magnesium carbonate, dried aluminum hydroxide gel, magnesium oxide, magnesium aluminate metasilicate, synthetic hydrotalcite and magnesium aluminum hydroxide, adding an enteric high molecular substance and a plasticizer optionally with a higher fatty acid ester to the resultant co-pulverized mixture, subjecting the mixture to co-pulverization and then dry-processing the co-pulverized product to a pharmaceutically acceptable solid form containing an effective vasodilating or hypotensive amount of nifedipine.

8. A solid nifedipine preparation according to claim 7, wherein the enteric high molecular substance is a member selected from the group consisting of cellulose acetate phthalate, hydroxypropylmethylcellulose phthalate, methyl methacrylate copolymer, polyvinyl acetate phthalate, cellulose acetate succinate and styrene-maleric acid copolymer.

9. A solid nifedipine preparation according to claim 7, wherein the plasticizer is a member selected from the group consisting of polyethylene glycol normally solid at room temperature, triacetin, polyoxyethylene sorbitan monooleate and propylene glycol acetylated monoglyceride.

10. A solid nifedipine preparation according to claim 7, wherein the higher fatty acid ester is a member selected from the group consisting of sucrose fatty acid ester, sorbitan fatty acid ester and glycerin fatty acid ester, in which the fatty acid moiety is derived from long chain fatty acids with 6–18 carbon atoms and the ester has an HLB value of 1–8.

11. A solid nifedipine preparation according to claim 7, wherein at least 0.5 part by weight of casein and 0.2–9 parts by weight of the inorganic excipients are used per part by weight of nifedipine and wherein at least 1 part by weight of the enteric high molecular substance and at lease 0.1 part by weight of the plasticizer are used per part by weight of the co-pulverized mixture.

12. A solid nifedipine preparation according to claim 7, wherein the higher fatty acid ester is present in an mount of 2% based on the mixture.

13. A solid nifedipine preparation according to claim 7, wherein the pharmaceutically acceptable solid form is a member selected from the group consisting of granules, tablets, dragees and capsules.

* * * * *